United States Patent
Morikawa

(10) Patent No.: US 7,550,080 B2
(45) Date of Patent: Jun. 23, 2009

(54) LIQUID CHROMATOGRAPH ANALYSIS APPARATUS AND METHOD

(75) Inventor: Tsuyoshi Morikawa, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 278 days.

(21) Appl. No.: 11/371,972

(22) Filed: Mar. 9, 2006

(65) Prior Publication Data

US 2006/0207941 A1 Sep. 21, 2006

(30) Foreign Application Priority Data

Mar. 18, 2005 (JP) .............................. 2005-079714

(51) Int. Cl.
*B01D 15/08* (2006.01)

(52) U.S. Cl. .................... 210/198.2; 210/101; 210/143; 210/656

(58) Field of Classification Search .............. 210/198.2, 210/656, 659, 96.1, 101, 143; 422/70
See application file for complete search history.

(56) References Cited

U.S. PATENT DOCUMENTS

| 5,393,434 | A  * | 2/1995  | Hutchins et al. | ............. 210/656 |
| 6,829,743 | B1 * | 12/2004 | Hongu et al.    | ............... 715/209 |
| 7,178,414 | B1 * | 2/2007  | Kokosa          | .................... 73/863.32 |
| 7,292,943 | B2 * | 11/2007 | Elder et al.    | .................... 702/14 |
| 2004/0008175 | A1 * | 1/2004 | Elder et al. | ................. 345/100 |
| 2005/0247625 | A1 * | 11/2005 | Liu et al. | .................... 210/635 |
| 2005/0278728 | A1 * | 12/2005 | Klementiev | ................. 719/328 |
| 2006/0005132 | A1 * | 1/2006 | Herdeg | ........................ 715/704 |
| 2006/0027490 | A1 * | 2/2006 | DeMarco | ................. 210/198.2 |
| 2006/0273011 | A1 * | 12/2006 | Larson | ........................ 210/656 |

FOREIGN PATENT DOCUMENTS

JP  2001-255316  9/2001

OTHER PUBLICATIONS

PTO 08-2916 Translation of Japan Patent No. 2001-255316.*

* cited by examiner

*Primary Examiner*—Ernest G Therkorn
(74) *Attorney, Agent, or Firm*—Rankin, Hill & Clark LLP

(57) ABSTRACT

A liquid chromatograph analysis apparatus includes: a macro storing section for storing a macro program having various commands related to a purge operation; a macro executing section for reading the macro program and analyzing and executing the program thus read; and a solvent database in which information on properties of solvents are stored. Based on information input by a user and the information stored in the solvent database, an optimum condition value is determined. Thus, a macro creating function for creating the macro program having operation commands based on the optimum condition value is provided. Further, the macro program can be instantly executed by operating a switch attached to the apparatus body.

6 Claims, 5 Drawing Sheets

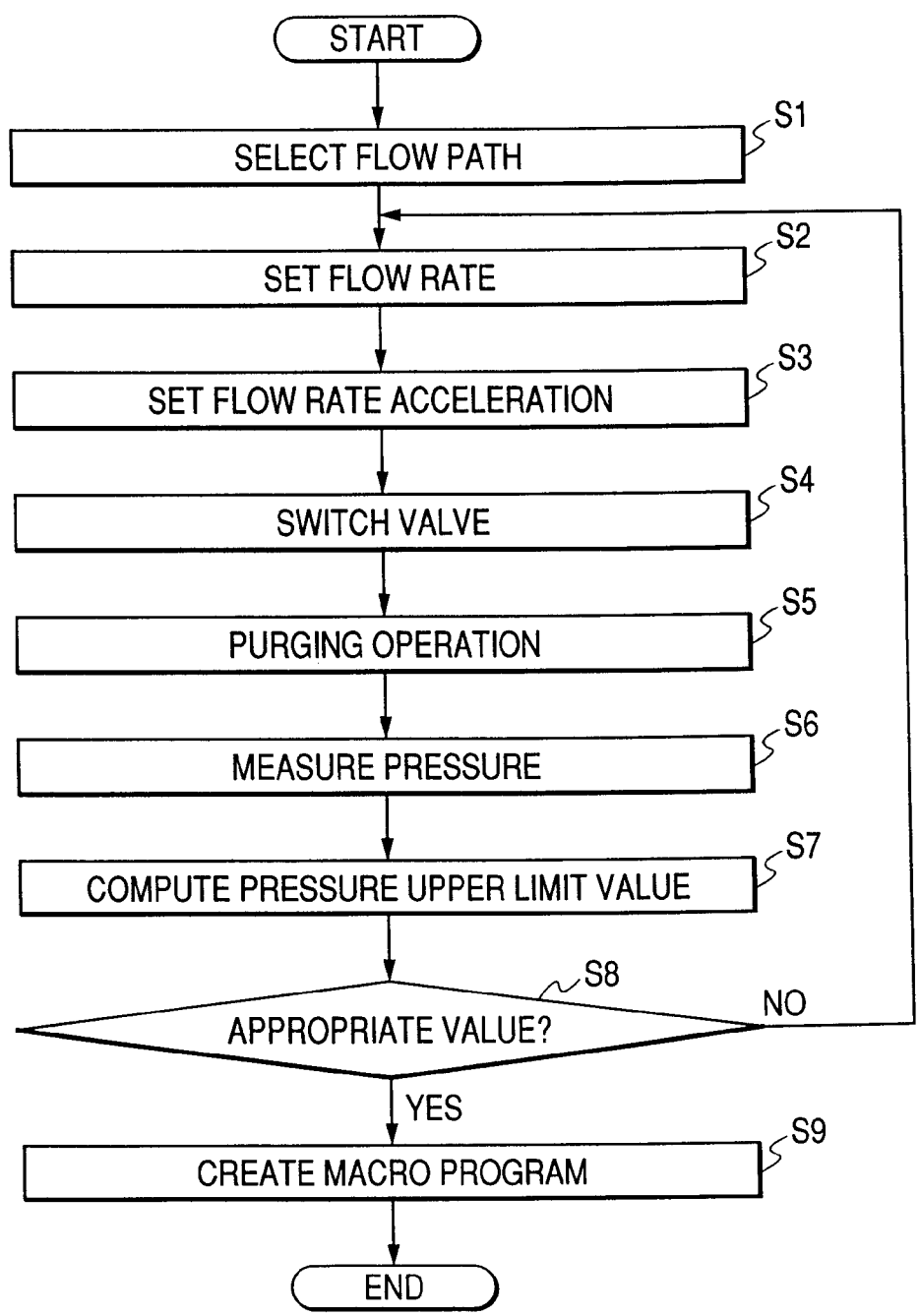

LIQUID CHROMATOGRAPH ANALYSIS APPARATUS AND METHOD

This application claims foreign priority based on Japanese Patent application No. 2005-079714, filed Mar. 18, 2005, the content of which is incorporated herein by reference in its entirety.

BACKGROUND OF THE INVENTION

1. Field of the Invention

This invention relates to a liquid chromatograph analysis apparatus and a liquid chromatograph analysis method.

2. Description of the Related Art

In the liquid chromatograph analysis apparatus, when an analysis is started or when a solvent is replaced, it is necessary to execute a purge operation for replacing liquid in a tube or removing air bubbles entered in the tube. In a related art, in doing such a purge operation, a user performing an analysis needs to manually operate a switching valve for switching between a main flow path for analysis and a discharge flow path for purging. Such a manual purge operation is troublesome for the user, and is a great obstacle to achieve a complete automated analysis by the liquid chromatograph.

However, in doing the purge operation, it is necessary to feed the liquid at a flow rate approximately equal to or greater than that in the main flow path. Therefore, in a case where the apparatus automatically switches the switching valve for switching between the main flow path for analysis and the discharge flow path for purging, a flow path pressure may reach a pressure upper limit value so that a system stops during the purging. In order to obviate such an inconvenience, a system using a dedicated hardware for managing a flow path length and a tube diameter is developed (for example, refer to JP-A-2001-255316).

However, in the case of the system using the dedicated hardware as described above, there is a problem that a flow path configuration is limited so as to simplify a control. In addition, it is difficult to realize the automated purging in a desired flow path configuration according to an analysis purpose. Further, in the system using the dedicated hardware, the flow path that can be automatically purged and the flow path that cannot be automatically purged are both provided.

Further, usually, in the liquid chromatograph analysis apparatus, an analysis file in which sample numbers, an analysis order, an analysis condition for each sample, and the like are defined is previously created by an user. By controlling respective sections of the apparatus according to the analysis file, the analysis is executed according to a desired procedure and condition. Therefore, even in the liquid chromatograph which is not equipped with the above dedicated hardware, by using such a function, it is possible to create the analysis file including operation commands for purging at a start and an end of a sequential sample analysis. The purge operation can be performed by executing the analysis file. However, since the purge operation in this case is performed as a part of analysis, at the utmost, the user cannot invoke a command for purging as required to execute the command instantaneously. Further, since measurement data is generated also while the purge operation is performed, a time and labor of deleting unnecessary measurement data are taken, and a problem may occur such that deleting of the data is forgotten.

Further, in an analysis using a buffer solution in which an ionic compound is dissolved as the solvent, frequently, a gradient system in which two or three types of liquids are used is employed, and one or two types of liquids are employed as cleaning fluid. In such a case, when the system remains in a state that the buffer solution is left in the flow path, for a long time, the ionic compound may be precipitated to block the flow path or the precipitated crystal may damage a seal or the like of a driving system. Further, the tube may be corroded. In order to obviate such an inconvenience, usually, where the analysis is not performed after the buffer solution is used, the buffer solution is replaced into a nonionic liquid so as to be stored. In this case, when a solubility of the ionic compound with respect to the replacing liquid is low, direct replacement of the buffer solution may cause the precipitation of the ionic compound, which may block the flow path. Thus, the purging using a plurality of liquids needs to be performed. In this case, the user needs to appropriately set a purging order and a mixing rate of the plurality of liquids. This requires certain knowledge and attention. As a result, only a skilled user can perform the appropriate setting.

Further, in the usual purge operation, the liquid replacement can be done in the flow path in an outlet of a liquid transfer section and in the flow path up to the in front of an analysis column. However, in the replacement between the liquids which are not miscible with each other and of which properties are completely different from each other, the liquid is not replaced sufficiently by the direct replacement. Therefore, after the replacement is performed with the liquid having an intermediate property of both liquids for all the flow paths, the replacement into a target liquid needs to be made. Thus, in such a case, the usual liquid feeding operation needs to be performed over all the flow paths during the purge operation. Accordingly, the automation of the liquid replacement is difficult to be realized.

SUMMARY OF THE INVENTION

An object of the present invention is to provide a liquid chromatograph analysis apparatus which can easily perform an automated purge operation under an appropriate condition according to a flow path configuration such as flow path length, tube diameter and number of flow paths, and property of a solvent.

In some implementations, a liquid chromatograph analysis apparatus of the invention comprises: an input section for inputting information; a macro creating section for creating a macro program based on the input information, the macro program defining an operating order and a condition value of each operation in a purge operation, the purge operation being performed on at least one of a high-pressure flow path and a low-pressure flow path; a macro storing section for storing the macro program; and a macro executing section for reading the macro program from the macro storing section, and analyzing and executing the macro program.

In accordance with the liquid chromatograph analysis apparatus according to the present invention having the configuration described above, the macro program having various commands related to the purge operation such as flow rate, flow rate acceleration, pressure upper limit value and control of a flow path switching valve during the purge operation is previously created, and the macro program thus created is executed. Accordingly, the purge operation can be automatically performed separately from a sample analysis. Incidentally, such a macro program may be created for each of the flow paths to be purged. Otherwise, the macro program including the command defining the procedure and the condition of the purge operation may be created for each flow path, and the macro program may be executed, thereby enabling the purging in plural types of the flow paths.

The liquid chromatograph analysis apparatus of the invention further comprises: a pressure measuring section for measuring a pressure in the at least one of the high-pressure flow path and the low-pressure flow path; a purge testing section for performing a test of the purge operation according to the condition value of each operation in the purge operation, the condition value being set based on the input information; and a condition value determining section for determining whether the condition value is appropriate based on a measurement result in the pressure measuring section while the test of the purge operation is performed in the purge testing section.

Further, as described above, when the liquid chromatograph analysis apparatus includes the pressure measuring section, the purge testing section and the condition value determining section, by setting an appropriate condition value such as the flow rate acceleration during the purging based on the information input by a user who performs the analysis, and by testing the purge operation at the condition value, it can be determined whether or not the condition value is appropriate based on the pressure of the flow path at that time. In this case, in a system having various flow path configurations, the macro program can be easily created under an optimum condition according to a flow path resistance determined by the flow path length, the tube diameter and the liquid to be used in the liquid chromatograph analysis apparatus.

The liquid chromatograph analysis apparatus of the invention further comprises: a solvent database for storing information related to properties of solvents, wherein the macro creating section determines an optimum operating order and an optimum condition value in the purge operation based on the input information and the information stored in the solvent database.

Further, where the liquid chromatograph analysis apparatus includes the solvent database as described above, the apparatus can automatically determine the optimum operating order and the optimum condition value based on the information input by the user and the information stored in the solvent database. In this case, the macro program having the command related to a purging order by a plurality of liquids and a mixing ratio of solvents can be easily created taking into consideration a precipitating condition of a buffer solution and miscibility among the solvents.

In the liquid chromatograph analysis apparatus of the invention, the input section executes a wizard by which a user inputs the information through an interactive window.

Further, when the input section has a wizard function, the user has only to execute the macro creating wizard and answer questions displayed on a window in an interactive manner so as to create the macro program.

The liquid chromatograph analysis apparatus of the invention further comprises: a switch for instructing the liquid chromatograph analysis apparatus to start the purge operation, the switch being provided mechanically or by a software, wherein a user operates the switch so that the macro executing section reads, analyzes and executes the macro program.

Further, when the liquid chromatograph analysis apparatus includes the switch for invoking the macro program for purging, the switch being provided mechanically or by software, the user can operate the switch as required thereby to make the apparatus perform the purge operation instantaneously.

In some implementations, a liquid chromatograph analysis method of the invention comprises: inputting information; creating a macro program based on the input information, the macro program defining an operating order and a condition value of each operation in a purge operation, the purge operation being performed on at least one of a high-pressure flow path and a low-pressure flow path; storing the macro program in a macro storing section; and reading the macro program from the macro storing section, and analyzing and executing the macro program.

BRIEF DESCRIPTION OF THE DRAWINGS

FIG. 3 is a flow chart showing an example of a method of creating a macro program in the liquid chromatograph analysis apparatus according to an embodiment the invention.

DESCRIPTION OF THE PREFERRED EMBODIMENTS

Now referring to embodiments, an explanation will be given of the best mode for carrying out the invention.

Figure 1:
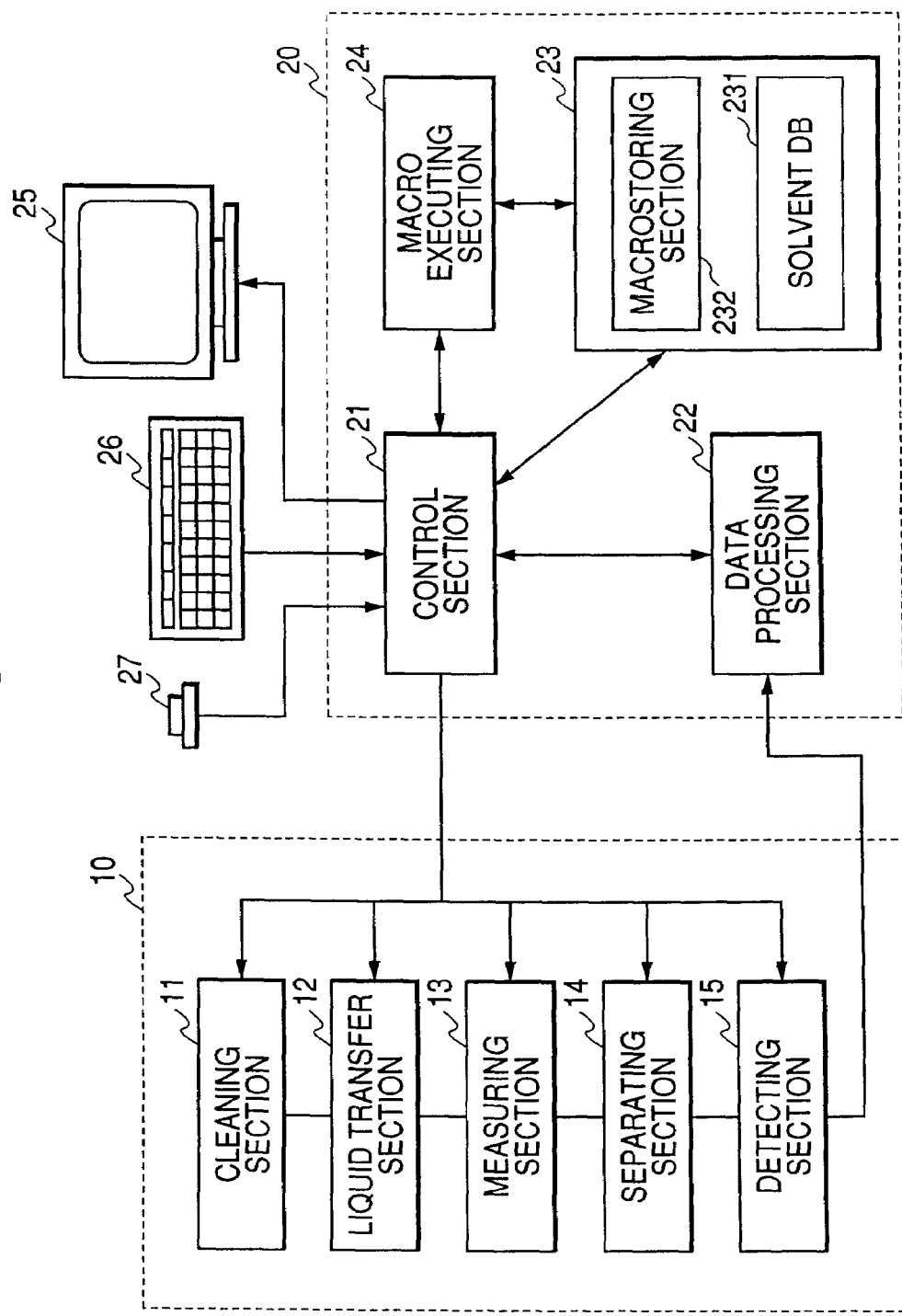
FIG. 1 is a schematic diagram showing an embodiment of a liquid chromatograph analysis apparatus according to the invention.
Figure 2A:
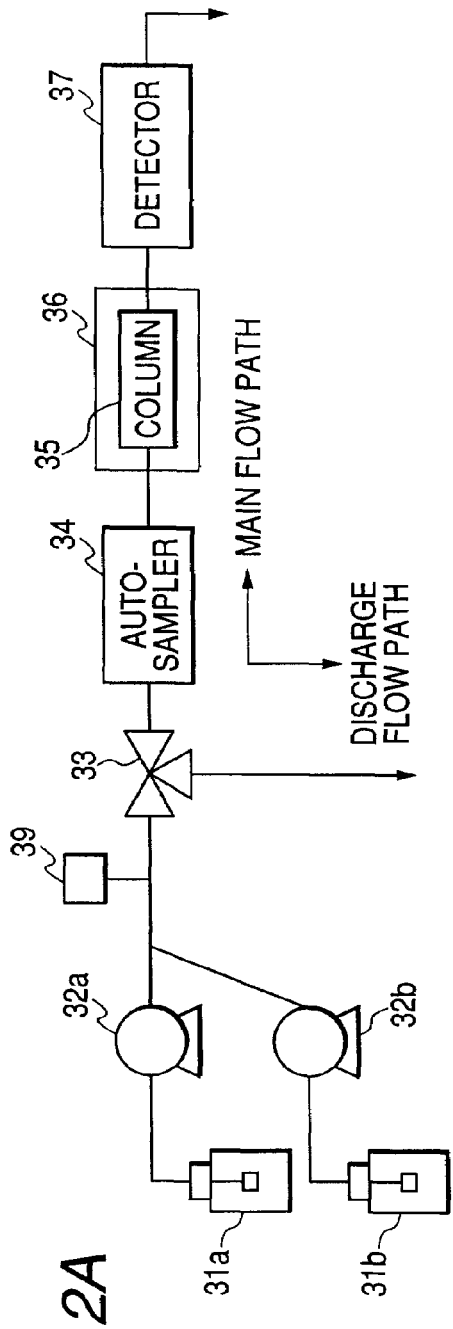
FIGS. 2A and 2B are schematic diagrams showing overall flow path configurations in the liquid chromatograph analysis apparatus according to an embodiment of the invention.
Figure 2B:
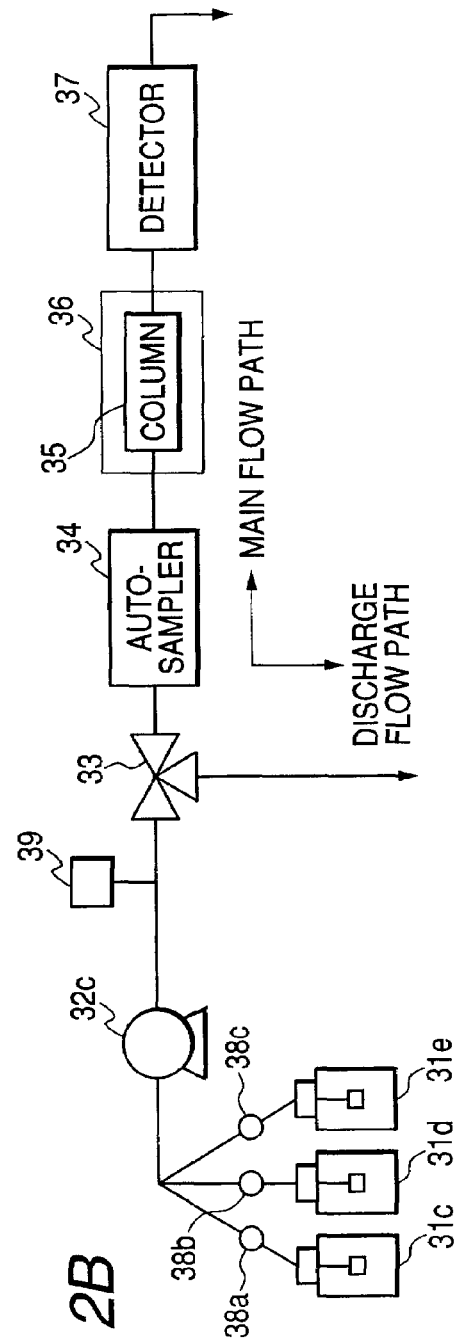

FIG. 1 shows a schematic configuration of a liquid chromatograph analysis apparatus according to an embodiment of the invention. FIGS. 2A and 2B show schematic configurations of flow paths in the liquid chromatograph analysis apparatus according to this embodiment. The liquid chromatograph analysis apparatus according to this embodiment mainly includes an analysis section 10 for performing an analysis operation and a control/processing section 20 for performing a control of the analysis section 10 and processing of measurement data.

The analysis section 10, as shown in FIGS. 2A and 2B, includes: a liquid transfer section 12 having solvent bottles 31$a$ to 31$e$, liquid feeding pumps 32$a$ to 32$c$ and the like; a measuring section 13 having an autosampler 34 equipped with a measuring pump, a sampling needle and the like; a separating section 14 having a column 35 and a column oven 36; a detecting section 15 having a detector 37 for detecting constituents being separated in terms of time in the separating section 14; and a cleaning section 11 having a cleaning pump for cleaning a tube, and the like.

Incidentally, FIG. 2A shows a high-pressure gradient system in which the plural solvent bottles 31$a$, 31$b$ are provided to the liquid feeding pumps 32$a$, 32$b$, respectively, and the solvents are mixed in a predetermined mixing ratio by controlling the respective flow rates of the pumps 32$a$, 32$b$. FIG. 2B shows a low-pressure gradient system in which the plural solvent bottles 31$c$ to 31$e$ and the single liquid feeding pump 32$c$ are provided, and the solvents are mixed in a predetermined mixing ratio by controlling opening/closing time of the valves 38$a$ to 38$c$ being provided to the solvent bottles 31$c$ to 31$e$, respectively, at a predetermined period.

Between the liquid feeding pumps 32$a$ to 32$c$ and the autosampler 34, a flow path switching valve 33 which is electrically controllable is provided. Using the switching valve 33, the flow path is changed between the main flow path for analysis and the discharge flowpath for purging. Further, between the liquid feeding pumps 32a to 32c and the switching valve 33, a pressure sensor 39 is provided respectively. Incidentally, in FIGS. 2A and 2B, only high-pressure flow paths for analysis are shown. However, the automatic purging by the liquid chromatograph analysis apparatus according to the present invention may be applied to not only the high-pressure flow paths but also to low-pressure flow paths such as the measuring section and the cleaning section when the switching valve is switched between the main flow path and the discharge flow path in each flow paths for the purpose of purging.

The control/processing section 20 includes a control section 21 for controlling the respective sections described above, a data processing section 22 for performing predetermined arithmetic processing based on a detected signal from the detecting section 15, a storage section 23 and a macro executing section 24. The control section 21 is connected to a display section 25 such as a monitor, and an input section 26 such as a keyboard and a mouse. An instruction from a user who performs analysis is transmitted from the input section 26 to the control section 21.

The storage section 23 includes: a solvent database 231 which stores various information related to a precipitation condition of a buffer solution and related to properties of solvents such as viscosity of each solvent and miscibility among the solvents; and a macro storing section 232 which stores a macro program including various commands for a purge operation. The macro executing section 24 analyzes the macro program read from the macro storing section 232, and makes the control section 21 to execute the macro program. Incidentally, the function of the control/processing section 20 can be realized by a general-purpose computer or the like that is installed with a predetermined computer program.

The control section 21 controls the liquid transfer section 12, the measuring section 13 or the cleaning section 11 so as to perform the purge operation. The control section 21 drives the flow path switching valve provided in a desired flow path (the high-pressure flow path for analysis, or the low-pressure flow path in the measuring section or the cleaning section) so as to switch the flow path from the main flow path to the discharge flow path for purging. Thereafter, the control section 21 drives the liquid feeding pumps, the cleaning pump or the measuring pump so as to transfer the liquid for purging. In this case, it is necessary to increase the flow rate at a predetermined flow path acceleration so that the flow path pressure does not drastically increase in the high-pressure flow path. Further, in order to prevent the pressure from excessively increasing due to clogging of the tube or the like, it is necessary to set a pressure upper limit value corresponding to a flow path resistance which depends on a flow path length or a tube diameter in the system, and a type of solution to be used. When the pressure exceeds the upper limit value, it is necessary to stop the liquid transfer for purging. Furthermore, when plural liquids are employed in the purging of each of the flow paths, it is necessary to determine a purging order and mixing ratio thereof by considering differences among the properties of the liquids.

In the liquid chromatograph analysis apparatus according to this embodiment, an operation procedure related to the above purge operation and a condition value related to each operation are defined in the macro program which is previously created. The macro program includes, for example, a control command of the valve correlated with the flow path, a command of setting the pressure upper limit value in purging, and a command of setting the purging flow rate and the flow rate acceleration. Further, where the purging is performed using the plural liquids, the macro program also includes a command of setting the optimum purging order and the optimum mixing ratio determined by considering the differences in the properties of the liquids. Incidentally, in setting the purging order and the mixing ratio in the purging using the plural liquids, the apparatus automatically determines the optimum purging order and the optimum mixing ratio based on the information related to the precipitation condition of the buffer solution and to the properties of the employed liquids, which are stored in the solvent database, according to the type of the solution to be used or the like that is input by the user.

The liquid chromatograph analysis apparatus according to this embodiment has a wizard function for creating the macro program described above. In creating the macro program, the user starts the macro creating wizard by a predetermined operation from the input section 26, and inputs a predetermined data according to an instruction in an interactive window displayed on the monitor 25. Based on the information input by the user and the information stored in the solvent database 231, the control section 21 determines the optimum value for each parameter related to the purge operation described above, and creates the macro program.

A detailed explanation will be given of the method for creating the macro program using the above macro creating wizard. FIG. 3 is a flow chart showing a method of creating the macro program according to the flow path resistance which depends on the flow path length or the tube diameter in the system, and the type of the solution to be used. First, when the user performs a predetermined operation through the input section 26 so as to start the macro creating wizard, a window which requests a selection of the flow path to be purged is displayed on the monitor 25. When the user selects the flow path to perform purging (S1) and performs a predetermined operation, subsequently, a window which requests a setting of the flow rate is displayed. When the user inputs an appropriate flow rate (S2), an initial flow rate acceleration is automatically set (S3). Next, the user drives the flow path switching valve of the flow path to be purged so that the flow path is switched from the main flow path to the discharge flow path for purging (S4) Then, the liquid transfer for purging is performed with the flow rate and the initial flow rate acceleration set as described above (S5). At this time, the pressure of the flow path is measured by the pressure sensor 39 (S6). By applying an operation margin to the flow path pressure thus measured, the pressure upper limit value is computed (S7). Further, whether or not the pressure upper limit value is appropriate is determined (S8). When the pressure upper limit value is not appropriate, the macro creation processing is returned to S2 again, and the process from setting of the flow rate to the determination of the pressure upper limit value is repeated. When the pressure upper limit value becomes an appropriate value, the macro program is created (S9).

Further, in the analysis in which the buffer solution with the ionic compound dissolved therein is employed as the solvent, due to the purging order to be subsequently executed and a concentration difference from that of the buffer solution in apart of the main flowpath where the purging is not performed, the ionic compound may precipitate, thereby blocking the flow path. For this reason, the purging order with the plural liquids and the mixing ratio of the plural liquids need to be suitably controlled.

Figure 4:
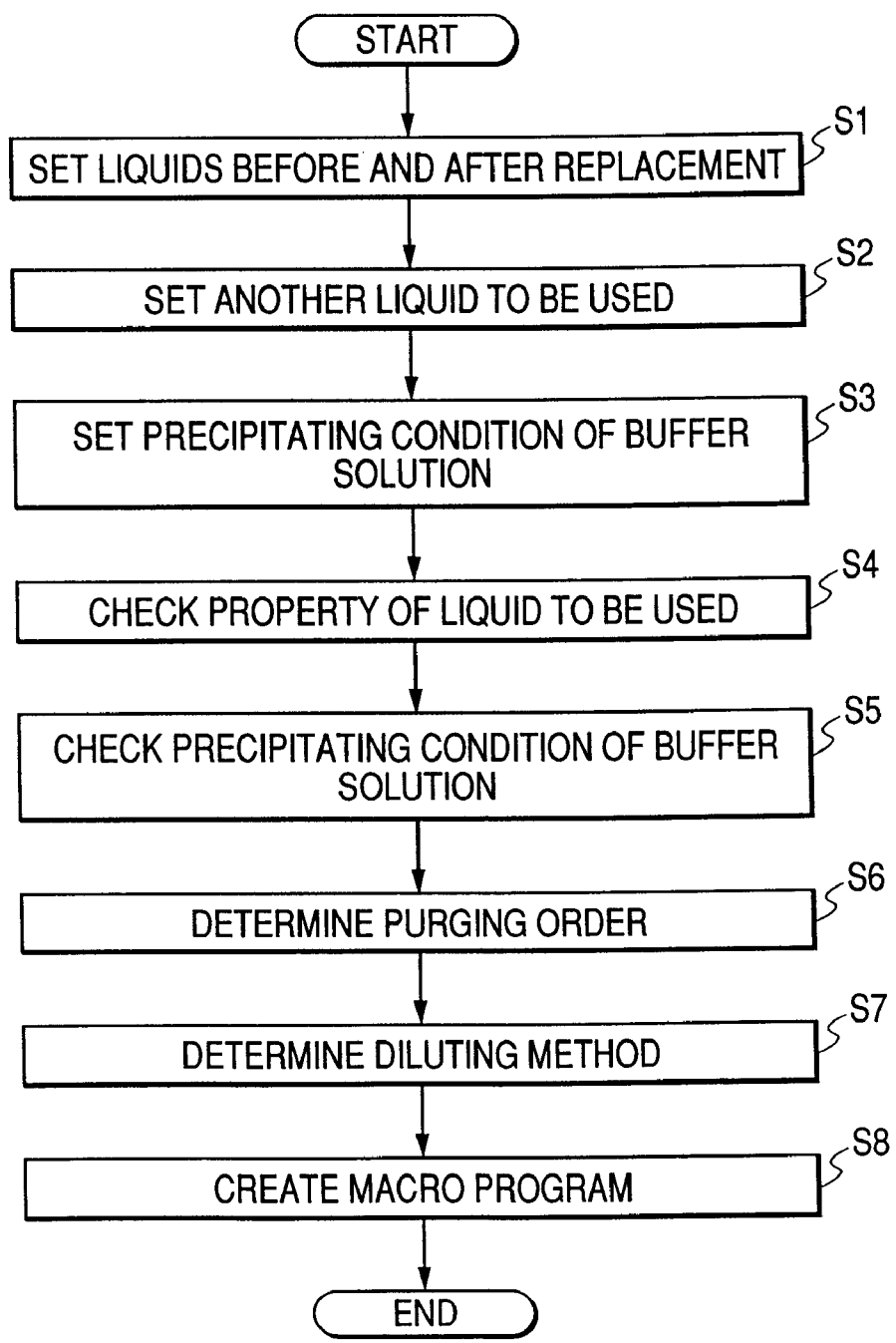
FIG. 4 is a flow chart showing another example of the method of creating the macro program in the liquid chromatograph analysis apparatus according to an embodiment of the invention.

FIG. 4 is a flow chart for showing a creating method of the macro program in the above case where the buffer solution with the ionic compound dissolved therein is employed. In this case, when the user performs a predetermined operation through the input section 26 after the macro program as described above is created, a window which requests a selection of the liquids before and after replacement is displayed on the monitor 25. When the user selects an appropriate liquid (S1), subsequently, a window which requests a selection of another liquid to be used, and a window which requests a setting of the precipitating condition of the buffer solution are displayed. When the user completes inputs in these windows (S2, S3), based on the information stored in the solvent database 231, the properties of the liquids to be used that are selected as above and the precipitating condition of the buffer solution are checked (S4, S5). Based on the checking result, the appropriate purging order is determined (S6). Then, a method for diluting the buffer solution by changing the mixing ratio over time is also determined (S7). Thus, the macro program is created (S8). Further, in this case, the following processing is desired. Namely, based on the information input by the user and the information stored in the solvent database, necessity of replacement in all the flow paths at the time of liquid replacement is determined. According to the necessity of the replacement in all the flow paths, a command for switching the flow path between the main flow path for analysis and the discharge flow path for purging is added to the macro program.

Further, in a case where the replacement is performed between the liquids which are not miscible with each other and of which properties are completely different from each other, other than the above buffer solution, similarly by using the macro creating wizard according to this embodiment, the macro program capable of setting the optimum parameters can be created.

The liquid chromatograph analysis apparatus according to this embodiment is provided with a mechanical switch 27 for invoking the above macro program so as to execute the macro program. When the user presses the mechanical switch 27, the macro program can be easily invoked and executed. Incidentally, the switch for invoking and executing the macro program is not limited to the mechanical switch but may be a software switch implemented in software. In this case, the user operates the software switch such as a button that is displayed on the monitor 25 through the input section 26 such as the mouse and the keyboard connected to the control section 21.

When the mechanical switch or the software switch is operated by the user, the macro program stored in the macro storing section 232 is read, analyzed and executed by the macro executing section 24. The macro executing section 24 executes the command embedded in the program according to a time sequence of the macro program, thereby instructing the control section 21 to perform the switching between the main flow path for analysis and the discharge flow path for purging, the setting of the flow rate, the flow rate acceleration and the pressure upper limit value in each flow path, and the purging order of the plural liquids, and the switching of their mixing ratio. According to this instruction, the control section 21 controls the liquid transfer section 12, the measuring section 13 or the cleaning section 11 so that the purge operation is performed under the appropriate condition.

Figure 5A:
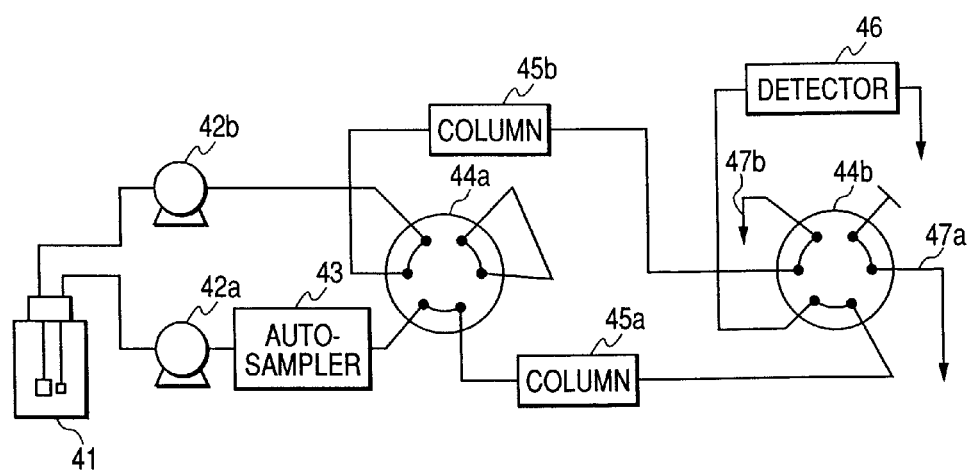
FIGS. 5A and 5B are schematic diagrams showing another embodiment of the liquid chromatograph analysis apparatus according to the invention.
Figure 5B:
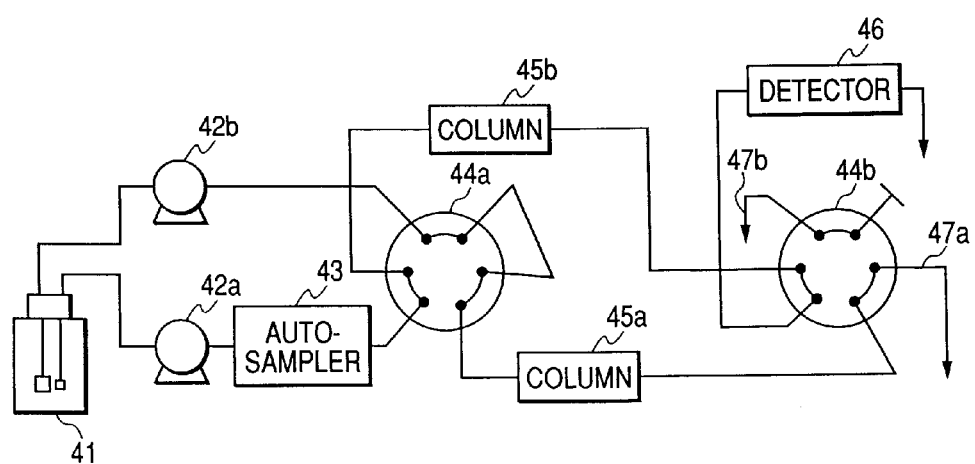

Further, the liquid chromatograph analysis apparatus according to this invention is not be limited to the system having the flow path configuration in this embodiment, but may be applied to the systems having various flow path configurations. For example, a system shown in FIGS. 5A and 5B has a flow path configuration in which a plurality of columns is provided and the analysis is performed in a certain column whereas the purging is performed for the other column.

This liquid chromatograph analysis apparatus includes a liquid feeding pump 42a for analysis, a cleaning pump 42b, two columns 45a, 45b, and two hexagonal valves 44a, 44b. Each hexagonal valve 44a, 44b can take a position A shown in FIG. 5A, and a position B shown in FIG. 5B that is rotated by 60 degrees from the position A. When the hexagonal valve 44a, 44b is in the position A, the column 45a is connected between the liquid feeding pump 42a for analysis and the detector 46 so that the analysis using the column 45a is performed. At this time, the column 45b is connected between the cleaning pump 42b and a drain 47b so that the column 45b is cleaned. On the other hand, when the hexagonal valve 44a, 44b is in the position B, on the contrary to the above case, the analysis is performed using the column 45b and the column 45a is cleaned. Also in the liquid chromatograph analysis having such a configuration, similarly as described above, by previously creating the macro program including the command for controlling the valve 44a, 44b, the command for setting the pressure upper limit value in the purging, and the command for setting the purging flow rate and the flow rate acceleration, and by executing this macro program, the purge operation can be easily performed under the appropriate condition.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A liquid chromatograph analysis apparatus comprising:
an input section for inputting information;
a pressure measuring section for measuring a pressure in at least one of a high-pressure flow path and a low-pressure flow path;
a purge testing section for performing a test purge operation in accordance with the inputted information;
a condition value determining section for determining an operating order and a condition value of each operation in a purge operation to be performed with respect to the at least one of the high-pressure flow path and the low-pressure flow path, based on the pressure measured in the test purge operation;
a macro creating section for creating a macro program based on the determined operating order and the condition value;
a macro storing section for storing the macro program; and
a macro executing section for reading the macro program from the macro storing section, and executing the macro program to perform the purge operation.

2. The liquid chromatograph analysis apparatus according to claim 1, further comprising:
a solvent database for storing information related to properties of solvents,
wherein the macro creating section determines an optimum operating order and an optimum condition value in the purge operation based on the input information and the information stored in the solvent database.

3. The liquid chromatograph analysis apparatus according to claim 1, wherein the input section executes a wizard by which a user inputs the information through an interactive window.

4. The liquid chromatograph analysis apparatus according to claim 1, further comprising:
a switch for instructing the liquid chromatograph analysis apparatus to start the purge operation, the switch being provided mechanically or by a software,
wherein a user operates the switch so that the macro executing section reads, analyzes and executes the macro program.

5. A liquid chromatograph analysis apparatus, comprising:
an auto sampler;
at least one switching valve disposed externally from the auto sampler, and one end of which is connected to the auto sampler, the switching valve operable to selectively cause one of a plurality of flow paths disposed externally from the auto sampler to communicate with the auto sampler;
an inputting section for inputting flow path information indicative of the one of the flow paths;
a macro creating section for creating, based on the information, a macro program defining an operating order and a condition value of each operation executed in a purge operation with respect to the one of the flow paths;
a macro storing section for storing the macro program; and
a macro executing section for reading the macro program from the macro storing section, and analyzing and executing the macro program.

6. The liquid chromatograph analysis apparatus according to claim 5, further comprising a solvent database for storing solvent information indicative of properties of solvents to be used in the liquid chromatograph analysis apparatus,
wherein the macro creating section determines an optimum operating order and an optimum condition value of the purge operation based on the flow path information and the solvent information.

* * * * *